(12) United States Patent
Navab et al.

(10) Patent No.: US 8,314,815 B2
(45) Date of Patent: Nov. 20, 2012

(54) VIRTUAL PENETRATING MIRROR DEVICE FOR VISUALIZING OF VIRTUAL OBJECTS WITHIN AN AUGMENTED REALITY ENVIRONMENT

(76) Inventors: Nassir Navab, München (DE); Christoph Bichlmeier, München (DE); Tobias Sielhorst, München (DE)

( * ) Notice: Subject to any disclaimer, the term of this patent is extended or adjusted under 35 U.S.C. 154(b) by 728 days.

(21) Appl. No.: 12/297,156

(22) PCT Filed: Apr. 11, 2007

(86) PCT No.: PCT/EP2007/003206
§ 371 (c)(1),
(2), (4) Date: Oct. 14, 2008

(87) PCT Pub. No.: WO2007/115826
PCT Pub. Date: Oct. 18, 2007

(65) Prior Publication Data
US 2010/0149213 A1 Jun. 17, 2010

(30) Foreign Application Priority Data
Apr. 12, 2006 (EP) .................................. 06007724

(51) Int. Cl.
*G09G 5/00* (2006.01)
*A61B 5/05* (2006.01)
(52) U.S. Cl. ......................... 345/633; 600/407; 600/424
(58) Field of Classification Search .................... 345/633
See application file for complete search history.

(56) References Cited

U.S. PATENT DOCUMENTS

| 6,628,977 | B2 | 9/2003 | Graumann et al. |
| 6,711,433 | B1 | 3/2004 | Geiger et al. |
| 2001/0007919 | A1 | 7/2001 | Shahidi |
| 2003/0073901 | A1* | 4/2003 | Simon et al. .................. 600/424 |
| 2005/0134461 | A1* | 6/2005 | Gelbman et al. ........... 340/572.8 |
| 2005/0203367 | A1* | 9/2005 | Ahmed et al. ................ 600/407 |
| 2005/0272991 | A1 | 12/2005 | Xu et al. |

FOREIGN PATENT DOCUMENTS

| WO | WO 00/56215 | 9/2000 |
| WO | WO 02/100284 | 12/2002 |
| WO | WO 2007/115824 | 10/2007 |
| WO | WO 2007/115826 | 10/2007 |

OTHER PUBLICATIONS

Ronald T. Azuma, "A Survey of Augmented Reality," Presence, Cambridge, MA, US, (Aug. 1997), pp. 1-48.
International Search Report for PCT/EP2007/003205.
International Search Report for PCT/EP2007/003203.
International Search Report for PCT/EP2007/003206.

\* cited by examiner

*Primary Examiner* — Kee M Tung
*Assistant Examiner* — Sing-Wai Wu

(57) ABSTRACT

A virtual penetrating mirror device for visualizing at least one virtual object within an augmented reality environment includes a tracking system tracking a plurality of markers attached to a tangible object, and a displaying device associated with at least one additional marker, characterized in that the displaying device displays a first view of the tangible object and at least one virtual penetrating mirror virtually reflecting a second view of the tangible object according to a localized position of the displaying device relative to the markers attached to the tangible object, wherein the virtual penetrating mirror is virtually disposed within the first view of the tangible object.

23 Claims, 7 Drawing Sheets

VIRTUAL PENETRATING MIRROR DEVICE FOR VISUALIZING OF VIRTUAL OBJECTS WITHIN AN AUGMENTED REALITY ENVIRONMENT

CROSS-REFERENCE TO RELATED APPLICATIONS

This application is a National Stage Application claiming the benefit of International Application No. PCT/EP2007/003206 filed on Apr. 11, 2007, the contents of which are herein incorporated by reference in their entirety.

BACKGROUND

1. Technical Field

The present invention relates to a method and to a virtual penetrating mirror device for visualizing virtual objects from arbitrary view points within an augmented reality environment, with substantial use in medical and industrial applications.

2. Discussion of Related Art

The prior art related to the present invention is disclosed for example in CA2425075, US2002082498, U.S. Pat. No. 6,963,454, U.S. Pat. No. 6,999,239, US2005195279/US2002191003 and allows trailing of augmented reality systems with different capabilities regarding displays, tracking system and camera devices as to insert virtual objects in ureal scene.

However, the limitation of these methods in the mentioned patents is the lack of ability to provide intuitive control of the virtual objects.

The benefit of additional information due to augmented reality systems for interaction and navigation is disclosed in US2006284791 where multiple users can move within a virtual world and use a personal digital assistant (PDA) and a microphone for communicating information, which is not recognized by a single user.

However, entire examination of virtual entity can not be performed by a single user satisfactorily.

In US2007035563 an invention is disclosed using augmented reality to guide the user to a target object. Therefore the user receives initialization information, including a target location and a source location corresponding and gets navigational hints visualized in a screen space of the spatially enabled display.

However, additional abstract objects are required to guide the user to the target object, which in this case are available as non controllable features.

In WO03060830 an invention is described to make unseen hazards visible to increase preparedness dealing with the situation at hand. Information about hazards is given by computer-generated two- and three-dimensional graphical elements.

A limitation of WO03060830 is that the risky region visualized due to the virtual object can be seen only from one single direction and hence potential risk of the hazard cannot be fully estimated.

In US2003003430 method and apparatus are presented for an augmented reality-based fire fighter training system using realistic looking virtual fire, smoke, and extinguishing graphics to create a realistic scenario. The user is able to navigate a virtual water stream to extinguish virtual flames. Steam is visualized when water reaches fire to enhance realism of visual feedback due to interaction.

However, this patent does not disclose interactive methods to get an overview on virtual objects within a particular, hazardous situation that facilitates decision for further situational reaction.

In US2005251030 and US2005203380 system and method for surgical instrument placement using an image based navigation system is disclosed. Path to the object of interest in the patient can be interactively planed.

However, the augmented image is only generated for the viewpoint of the surgeon. Therefore regarding the surgical scenario disclosed in the mentioned patent, the possible surgeon's point of view on the operation site is restricted due to surrounding clinical staff, equipment in the operating room and the patient.

In DE10201116 a make-up mirror that can be attached to a PC monitor housing is described. Also an electronic mirror displayed on the monitor screen is mentioned, which is called "virtual mirror".

However, this patent does not proclaim an augmented realty scenario where the user interacts with virtual objects integrated into a real scene.

US2003128182 discloses a virtual mirror. This patent proclaims a mirror providing additional virtual information concerning the environment of a car while driving. A virtual mirror is rendered on a computer graphics display or screen. The display substantially replicates the optical properties of a physical mirror. The display is provided on a host mobile body. Accessing a geospatial database, US2003128182 describes a virtual mirror displaying items that would be seen in a mirror with an unobstructed view based on information of the position of the mobile body and display data indicative of items in proximity to the mobile body.

The limitation of US2003128182 as being geospatially oriented is that it is not suitable for applications requiring interactivity in personal space as it is the case for surgical operations and service and/or maintenance procedures on industrial components or products.

The proposed invention is not applicable to a medical or an industrial augmented reality environment.

A further limitation of US2003128182 is that the virtual object can be seen only from one single direction related to the actual position of the mobile body. The proposed mirror in US2003128182 therefore does not allow the virtual object to be seen from any arbitrary point of view, for example from the beneath, upon or behind in regard to the viewing direction.

One further limitation of US2003128182 is that the reflected object is only an approximation of the item intended to be mirrored.

The increasing amount of data provided by medical 3D imaging devices to surgeons makes new visualization technology necessary that reveal more information at a glance other than a stack of 2D slices. Visualizing-3D imaging data is less cumbersome than browsing through these stacks. As opposed to 2D images 3D data does not have a direct representation on a screen, hence it needs a recalculation to visualize it.

Ideally, the visualizations are embedded into the context of their use and not far away from the operation site as in current practice.

In order to take full advantage of the spatial relations in the 3D data, visualizations must convey the spatial information. The information perpendicular to the viewing direction is commonly preserved, however the absolute and relative depth information is gone on an ordinary 2D display. A promising technology for overcoming some of these shortcoming is augmented reality.

Augmented Reality for intra-operative 3D-visualization and navigation has been a subject of intensive research and development during the last decade. For example in U.S. Pat. No. 6,891,518 and U.S. Pat. No. 6,919,867 a basic system and method for visualization in an augmented reality environment is disclosed.

BRIEF SUMMARY

The objectives of the present invention are to remove the lack of ability to provide intuitive control of the viewing of the virtual object such that the said disadvantages of the known arrangements are avoided and to improve the ability of examination of complex structured virtual entities and to avoid the necessity of additional abstract objects to guide the user to the target object and to avoid a further disadvantage namely the restricted perception of the extent of the visualized sensitive regions due to occluding virtual objects and to remove the existing limitations on user interaction and to remove the limitation of having only restricted field of view onto the augmented reality scene and the lack of misleading perception of the relative and absolute distances of the objects in an augmented reality scene and to remove the lack of the access to an augmented reality environment as a personal space and to remove the lack of the ability to get any arbitrary perspectives onto the virtual object from the observer's point of view and finally to remove the disadvantage that the reflected object is only an approximation of the item intended to be mirrored.

The current invention achieves these objectives using a virtual penetrating mirror device for visualizing virtual objects within an augmented reality environment by presenting at least a virtual mirror and at least a virtual object on a display of a displaying device, which can be for instance a head mounted display, that provides an image of the virtual object, an image of the virtual mirror and an image of the reflected virtual object by the virtual mirror. Whereby the Virtual penetrating mirror device is able to handle any kind of virtual objects including those ones exactly reconstructed from real objects for example patient's anatomy reconstructed through 3D medical imaging.

The virtual mirror can be tangible by means of a tracked interaction device. Any additional abstract objects to guide the user to the target object are not necessary as mirrors are well-known devices in our everyday life. Using the reflection for navigational tasks, exploring physically restricted regions and understanding complex structures is intuitive and as easy as handling a real mirror.

A further improvement is that the virtual object reflected in the virtual mirror can be visualized in-situ, for instance virtual anatomy visualized from medical imaging data can be registered with a patient and positioned at its designated location. For planning an intervention in some cases only one view on the region of interest is not sufficient. In this case the virtual mirror provides arbitrary views on an operation site to understand for instance an anatomy and increase the perceptual information regarding absolute and relative distances of objects and reduce the risk of eventual errors.

Virtual objects can be presented as models based on surfaces. Furthermore volume data can be rendered using techniques of direct and indirect volume rendering. For indirect volume rendering boundaries of homogenous regions within volumetric data are detected and represented with surfaces. Real-time direct volume rendering techniques use so-called transfer functions to assign photometric parameters to each voxel, e.g. color and transparency. The term 'real-time' is defined with regard to the duration of a process in the real world. In terms of computer graphics applications, real-time rendering means around 30 frames per second. As a further advantage the virtual mirror is capable of visualizing digitally reconstructed radiographs (DRR) from 3D Computer Tomography (CT) volumes with arbitrary positioned x-ray sources defined by the varying viewpoint of the observer. Manipulation of the virtual object consisting in this case of preoperative CT data or modification of position and orientation of the virtual mirror, or the point of view of the observer results in a visualization of the sum of attenuation coefficient along the optical rays in the viewing volume of X-ray source within the body of the virtual object reflected on the virtual mirror.

An augmented reality scene presented on a display of a displaying device, which consists of at least one virtual mirror and further virtual objects reflected in the virtual mirror can be presented in real-time. Motion of the virtual mirror, the reflected virtual objects and the view point does not limit real-time capabilities of the visualization. The virtual objects can be observed from any arbitrary view point, which eases the examination of complex structured virtual entities.

The virtual object with the related image of the reflected virtual object by virtual mirror on display can be unrestrictedly positioned within an augmented reality scene. This also includes positions inside a real body for instance visualized anatomy in a real patient.

Furthermore the virtual mirror provides visual and proprioceptual information in a personal space about absolute and relative distances between objects within an augmented reality scene. The design of the virtual mirror is interactively modifiable by means of transforming the mirror image for metric scaling of the reflected image of the virtual object in the virtual mirror. Variable design parameters include size, color, shape, background of the image of the reflected virtual object and color of the image of the reflected object presented on the virtual mirror. The virtual mirror can be positioned and orientated in any scale without any restriction within the augmented reality scene. Furthermore the virtual mirror can be moved to positions inside real objects in an augmented reality scene.

A tracking system, which can be an optical tracking system spatially localizes the body, the tracked interaction device and the display device in the same coordinate system in real-time. Each tracked object is equipped with a tracking body, which can for example be an optical tracking target consisting of retro reflective markers.

The position of the virtual object is registered and superimposed with the body tracked by the tracking system. The virtual mirror can be virtually attached to the tracked interaction device localized by the tracking system and guided as intuitively within an augmented reality scene. The tracked interaction device can also be a mouse, a keyboard, a pedal or any other kind of switches or steering and control units.

The virtual mirror can reflect any virtual scene, which can include further virtual mirrors.

BRIEF DESCRIPTION OF THE DRAWINGS

The invention will now be elucidated by reference to the embodiment partially illustrated schematically in the drawings regarding an exemplary augmented reality scenario.

DETAILED DESCRIPTION OF EXEMPLARY EMBODIMENTS

Figure 1:
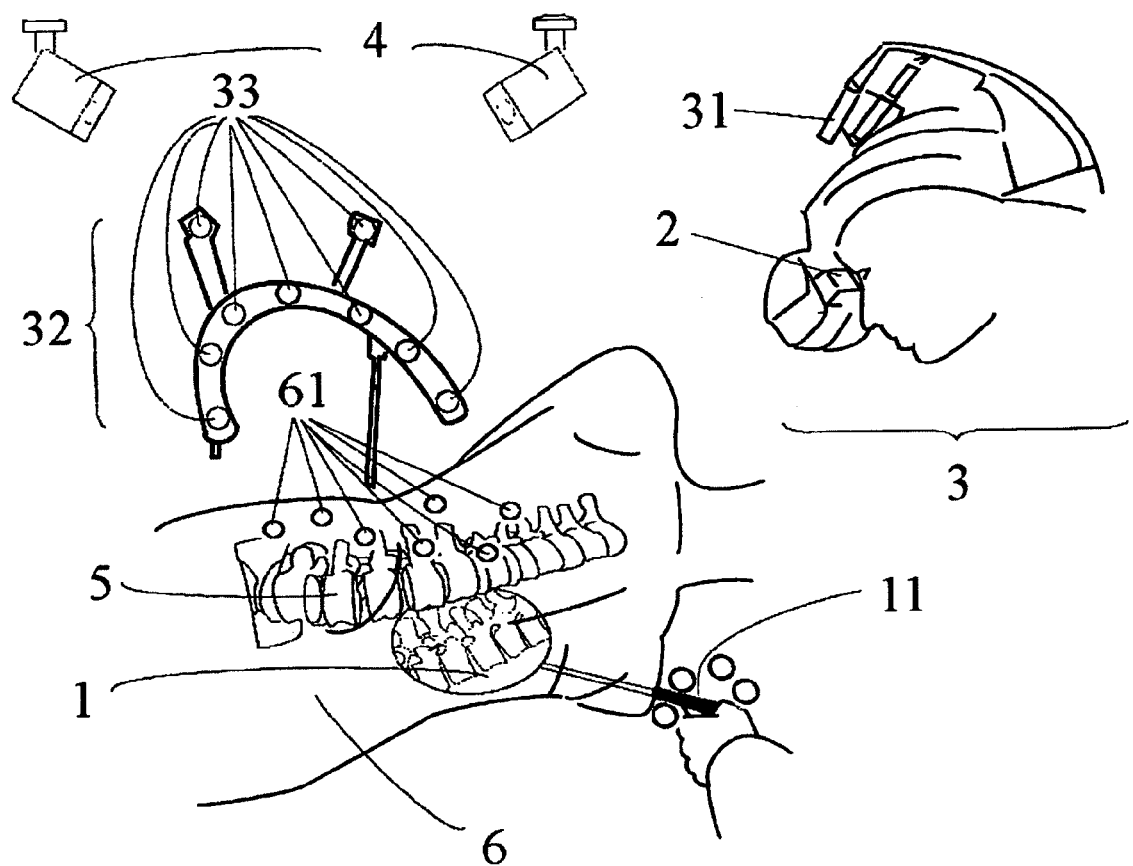
FIG. 1: a schematic view of an exemplary augmented reality scene with required hardware set up.

FIG. 1 shows an exemplary augmented reality scenario including a hardware set up having a tracking system 4 and a displaying device 3. The tracking system 4 localizes marker sets of tracking targets. Tracking targets are the body 6 with attached markers of the body 61, the tracked interaction device 11 and the tracking target related to displaying device 32 with attached markers related to displaying device 3. The augmented reality scene is presented with the display of the displaying device 2, which can be for instance the display of a head mounted display device or a monitor or a projector.

One tracking sensor for instance an infrared camera of the camera set of displaying device 31 tracks the tracking target related to displaying device 32 to estimate pose of the displaying device 3 to present the augmented reality scene from the observer's point of view 31 on the display of the displaying device 2. The virtual mirror 1 is intuitively controllable due to the tracked interaction device 11 and moves according to the motion of the observer. Visual feedback due to the image of the reflected virtual object by the virtual mirror on display 15 provides perceptual information about relative and absolute distances of virtual objects. When the view point 31, the virtual mirror 1 and the virtual object 5 is in motion, information about relative and absolute distances due to visual, perceptual cues and additional proprioceptual cues is enhanced.

The display of the displaying device 2 can also be a monitor, which is positioned independently from the observer somewhere in his or her field of vision. Therefore video images of the real scene can be captured by any camera device tracked by the tracking system 4.

The virtual part of the augmented reality scene consisting of the virtual mirror 1, the image of the virtual handle of virtual mirror on display 15 (shown in FIG. 4) and the virtual object 5 can only be seen in the display of the displaying device 2.

Figure 2:
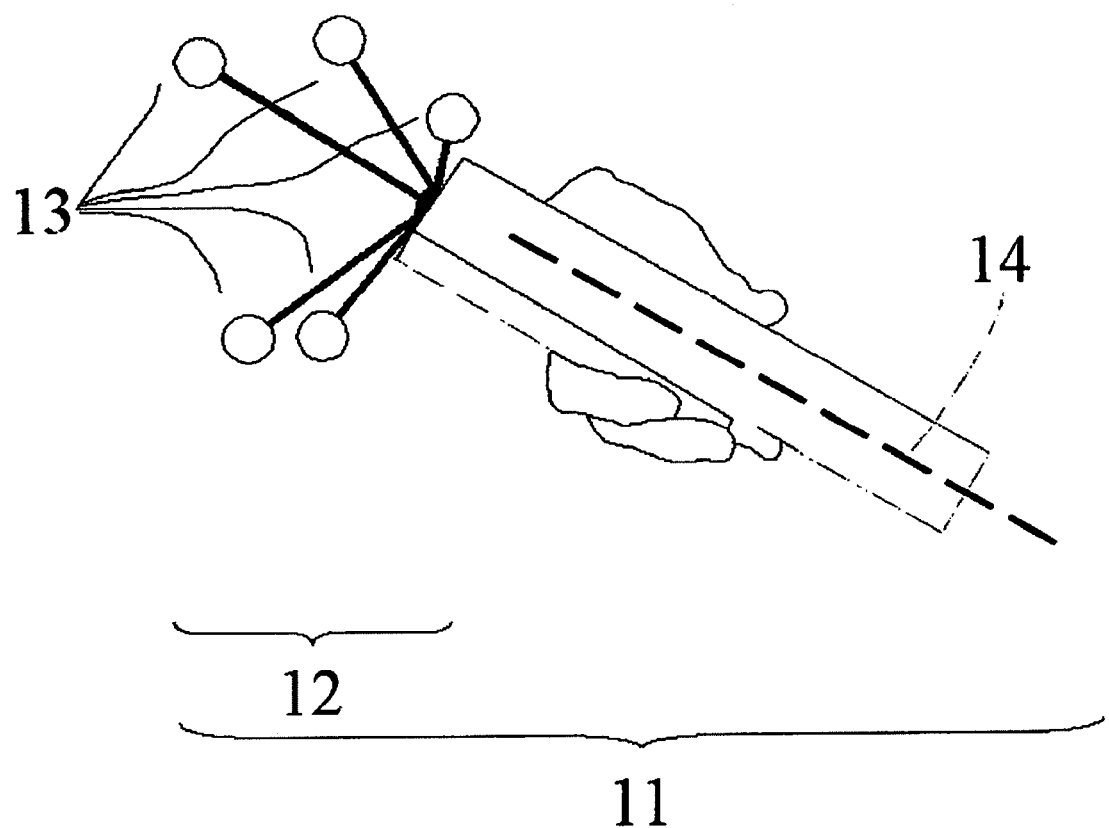
FIG. 2: a schematic view of an exemplary tracked interaction device.

FIG. 2 shows a tracked interaction device 11 with the attached tracking target of tracked interaction device 12, which is localized with the tracking system 4. The tracking target of tracked interaction device 12 consists of markers of tracked interaction device 13. The position and orientation of the virtual mirror 1 is controlled with the position of the tracked interaction device 11 and the orientation of the axis of tracked interaction device 14.

Figure 3:
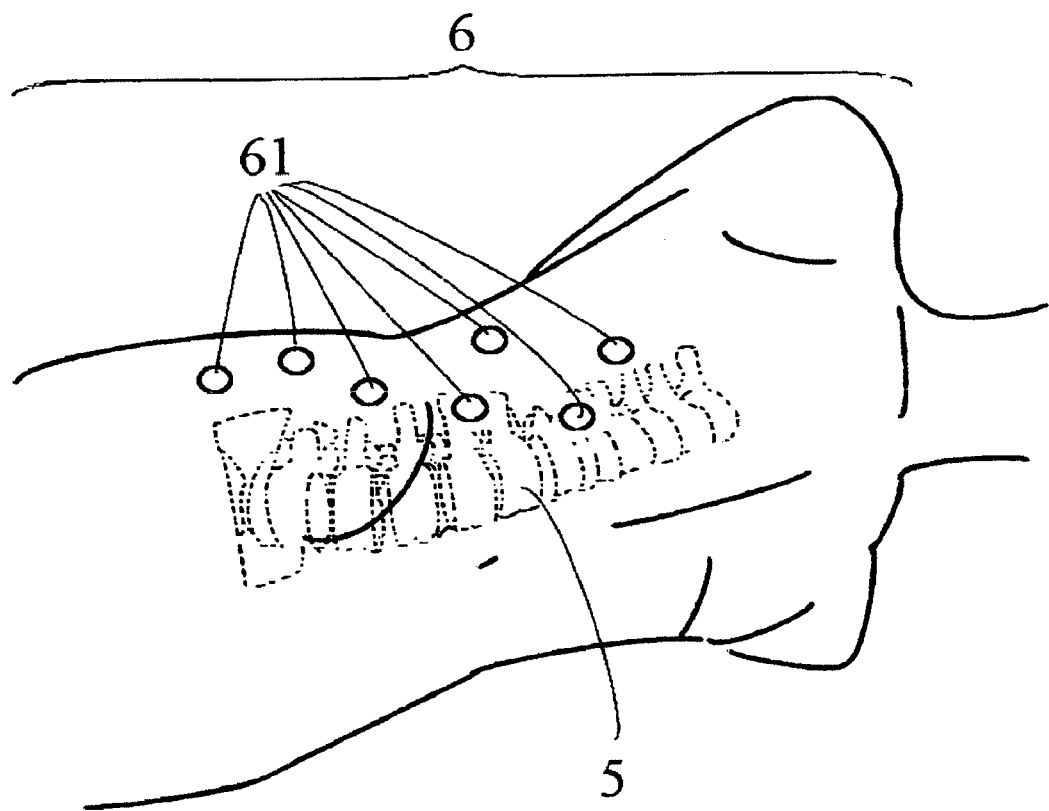
FIG. 3: a schematic view of an exemplary tracked body.

FIG. 3 shows the direct view on the tracked body 6 with attached markers of body 61 without using the displaying device 3. The virtual object 5 is completely surrounded and occluded by the body 6 and hence can not be seen directly without using the images presented on the display of the displaying device 2.

Figure 4:
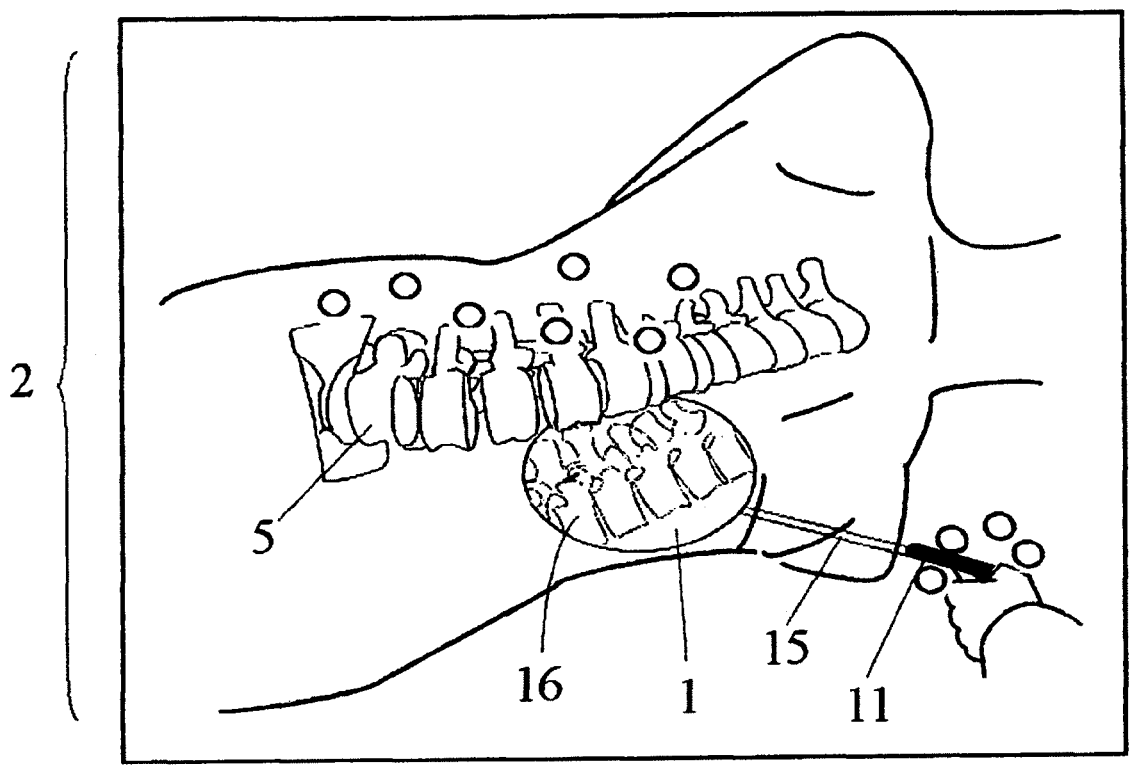
FIG. 4: a schematic view onto a display exemplary of a displaying device.

FIG. 4 shows an exemplary view on the display of the displaying device 2, which provides the view behind the real body 6 on the virtual object 5. In addition to the virtual object 5 the virtual mirror 1 is visible and provides an image of the reflected virtual object 16. The virtual minor 1 can be navigated through the augmented reality scene by a tracked interaction device 11. The tracked interaction device 11 is virtually connected with the virtual mirror 1 due to the virtual handle of the virtual minor 15. In addition to the direct view from the view point 31, which is in general limited, virtual mirror 1 provides any arbitrary view on the virtual object 5. In a medical augmented reality the virtual mirror 1 allows for instance perspectives on the operation site consisting of the virtual object 5 from beneath the operating table. The virtual mirror 1 can be moved to any arbitrary location, which includes moving the virtual mirror 1 also through real objects 6 and virtual objects 5. This liberty of interaction allows for detailed examination of complex structures, which can not be seen satisfactorily directly from the view point 31. Regarding medical augmented reality, examination of high risk regions at the operation site the virtual minor 1 provides any desired view and therefore supports decision making for the next step of the intervention and reduces eventual mistakes.

Mirrors are well-known devices in our everyday life. We are accustomed to interact and navigate with mirror reflection. Integration of the virtual mirror 1 avoids the application of additional abstract objects to navigate and guide the user through an augmented reality scene to a target object. Regarding for instance a medical augmented reality scene, a virtual surgical instrument can be intuitively guided to the operation site at a virtual object 5 using the direct view 31 and additional perspectives due to one or more virtual minors 1. Furthermore, the image of the reflected virtual object by virtual mirror on display 16 is the exact counterpart of the virtual object 5, which improves the ability of recognizing the image of the reflected virtual object by the virtual mirror on display 16 and enhances intuitiveness of interaction.

Figure 5:
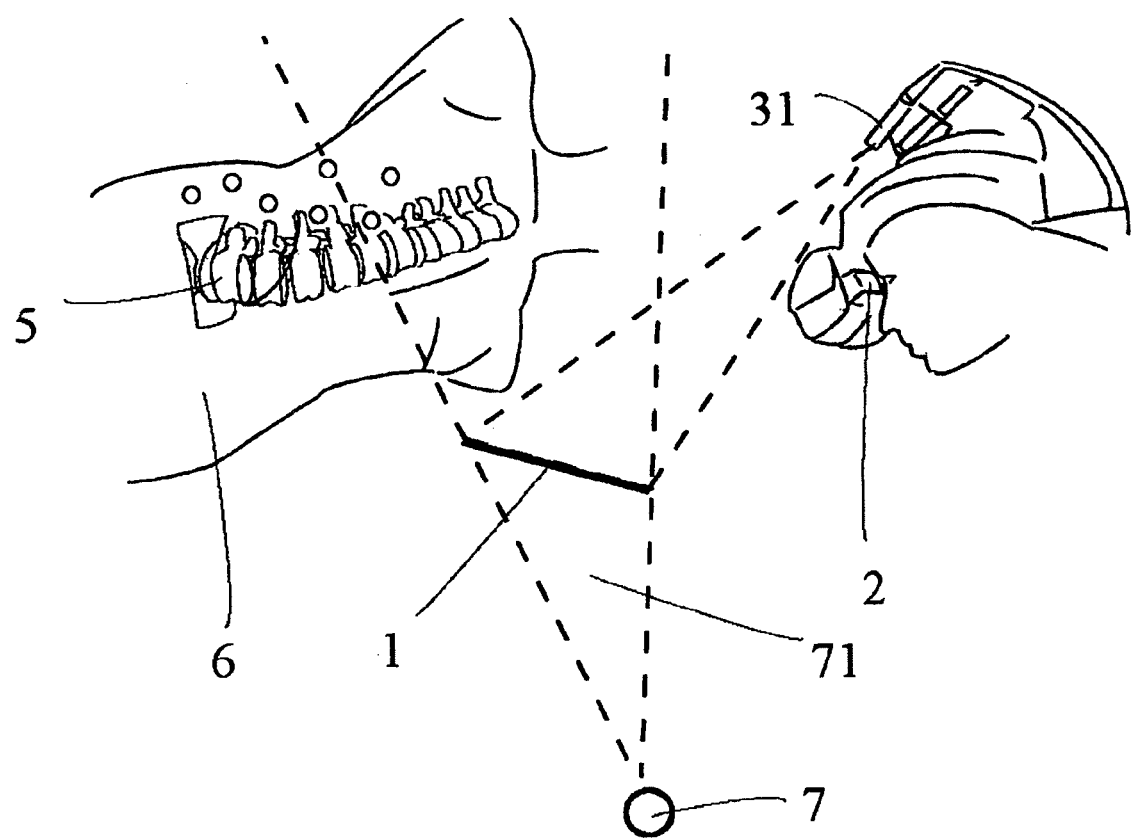
FIG. 5: a schematic view of generation of arbitrary x-ray sources.

FIG. 5 shows the generation of arbitrary x-ray sources 7 showing digitally reconstructed radiographs (DRR) using the virtual minor 1. The view volume of X-ray source 71 of the x-ray source 7 can be defined by adjusting the position of the virtual mirror 1, the view point 31 of the displaying device 3 and the virtual object 5. The observer sees from the view point 31 the sum of attenuation coefficient along the optical rays in the view volume of X-ray source 71 within the body of the virtual object 5 reflected on the virtual mirror 1.

Figure 6:
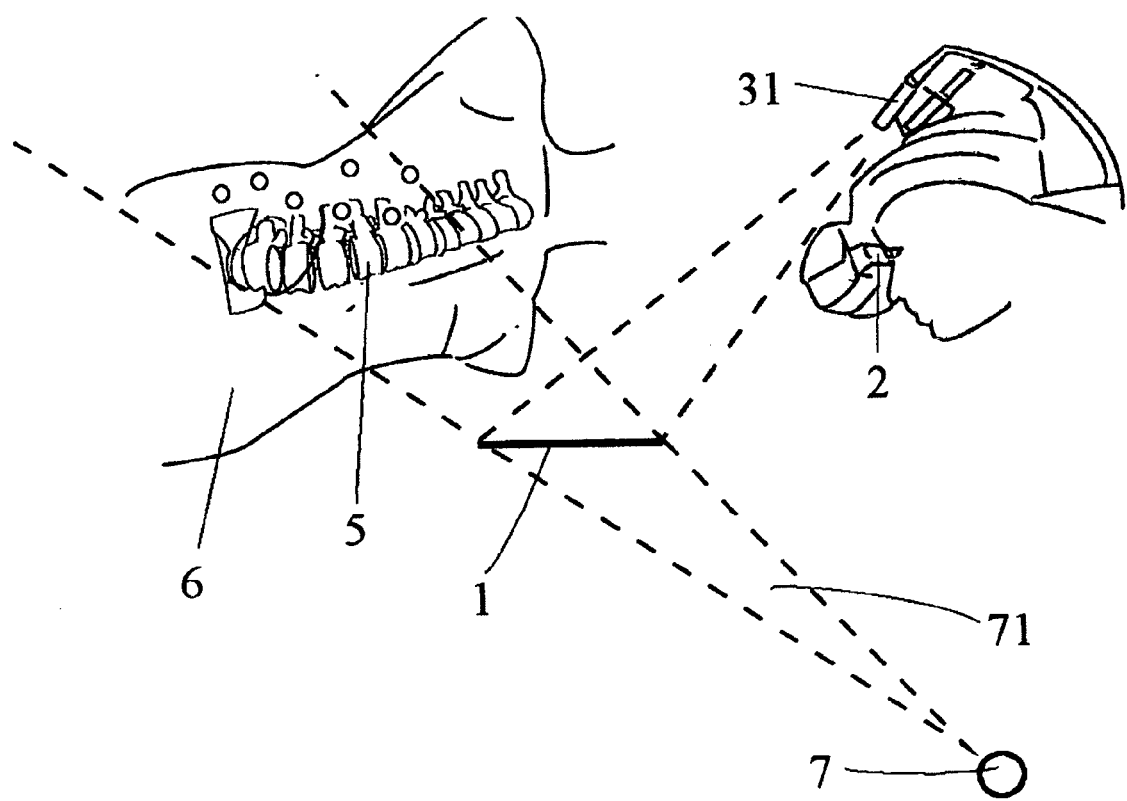
FIG. 6: a schematic view of generation of arbitrary x-ray sources.

The schematic view of FIG. 6 differs from FIG. 5 in that the angular position of the virtual mirror 1 is changed and hence another portion of the virtual object 5 is reflected on the virtual mirror 1.

Figure 7:
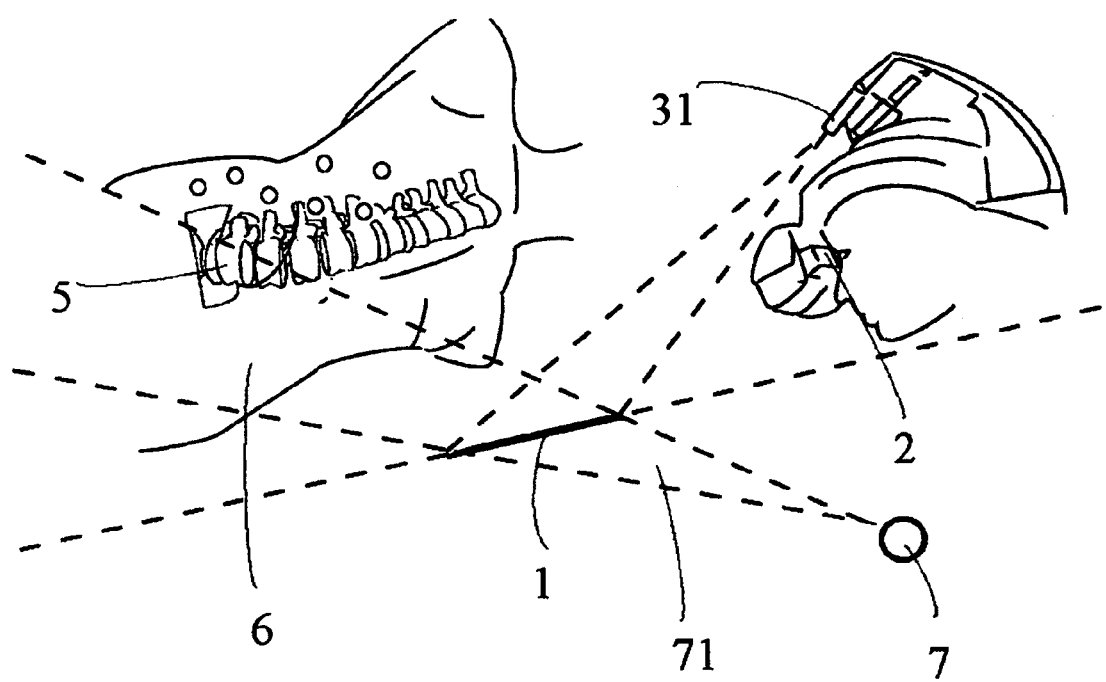
FIG. 7: a schematic view of generation of arbitrary x-ray sources.

The schematic view of FIG. 7 differs from FIGS. 5 and 6 in that the angular position of the virtual mirror 1 is further changed and hence another portion of the virtual object 5 is reflected on the virtual mirror 1 differing from those of the FIGS. 5 and 6.

REFERENCE LIST OF DRAWINGS 1 virtual mirror
11 tracked interaction device
12 tracking target of tracked interaction device
13 markers of tracked interaction device
14 axis of tracked interaction device
15 image of the virtual handle of virtual mirror on display
16 image of the reflected virtual object by virtual mirror on display
2 display of displaying device
3 displaying device
31 view point
32 tracking target related to displaying device
33 markers related to displaying device
4 tracking system
5 virtual object 6 body
61 markers of body
7 X-ray source
71 view volume of X-ray source

The invention claimed is:

1. A virtual penetrating mirror device for visualizing at least one virtual object within an augmented reality environment, the virtual penetrating mirror device comprising:
    a tracking system tracking a plurality of markers attached to a tangible object; and
    a displaying device associated with at least one additional marker, characterized in that the displaying device displays a first view of the tangible object and at least one virtual penetrating mirror virtually reflecting a second view of the tangible object according to a localized position of the displaying device relative to the markers attached to the tangible object, wherein the virtual penetrating mirror is virtually disposed within the first view of the tangible object.

2. The virtual penetrating mirror device according to claim 1, characterized in that the virtual penetrating mirror displays the second view penetrating into the tangible object.

3. The virtual penetrating mirror device according to claim 1, characterized in that the second view of the tangible object is displayed in-situ.

4. The virtual penetrating mirror device according to claim 1, characterized in that the virtual penetrating mirror virtually reflects surfaces of the tangible object occluded in the first view.

5. The virtual penetrating mirror device according to claim 1, characterized in that the virtual penetrating mirror virtually reflects rendered volumes.

6. The virtual penetrating mirror device according to claim 1, characterized in that the virtual penetrating mirror virtually reflects a digitally reconstructed radiograph image.

7. The virtual penetrating mirror device according to claim 1, characterized in that the virtual penetrating mirror virtually reflects images of the tangible object, in real time with a relative movement of the another marker and the plurality of markers.

8. The virtual penetrating mirror device according to claim 1, characterized in that the reflected second view is aligned and superimposed onto an image of the tangible object.

9. The virtual penetrating mirror device according to claim 1, characterized in that the virtual penetrating mirror is interactively variable.

10. The virtual penetrating mirror device according to claim 1, characterized in that the shape of the virtual penetrating mirror is interactively variable.

11. The virtual penetrating mirror device according to claim 1, characterized in that the virtual penetrating mirror virtually reflects an image of the tangible object in any scale.

12. The virtual penetrating mirror device according to claim 1, characterized in that a size of the virtual penetrating mirror is scalable.

13. The virtual penetrating mirror device according to claim 1, characterized in that a color of the image is interactively variable.

14. The virtual penetrating mirror device according to claim 1, characterized in that a color of a background of the image is interactively variable.

15. The virtual penetrating mirror device according to claim 1, characterized in that a color of the virtual penetrating mirror is interactively variable.

16. The virtual penetrating mirror device according to claim 1, characterized in that an interaction with the virtual penetrating mirror provides visual perceptual information about absolute and relative distances between objects within an augmented reality scene.

17. The virtual penetrating mirror device according to claim 1, characterized in that an interaction with the virtual penetrating mirror provides proprioceptual perceptual information about absolute and relative distances between objects within an augmented reality scene.

18. A virtual penetrating mirror device for visualizing at least one virtual object within an augmented reality environment, the virtual penetrating mirror device comprising:
    a tracking system tracking a plurality of markers attached to a tangible object;
    a displaying device; and
    a tracked interaction device associated with at least one additional marker, characterized in that the displaying device displays a first view of the tangible object and at least one virtual penetrating mirror virtually reflecting a second view of the tangible object according to a localized position of the tracked interaction device relative to the markers attached to the tangible object, wherein the virtual penetrating mirror is virtually disposed within the first view of the tangible object.

19. The virtual penetrating mirror device according to claim 18, characterized in that the tracked interaction device provides rotational angle and metric movement of the virtual penetrating mirror relative to the markers attached to the tangible object.

20. A method for visualizing a virtual object within an augmented reality environment comprising:
    localizing a tangible object relative to a tracking system;
    localizing a displaying device relative to the tracking system; and
    displaying by the displaying device a first view of the tangible object and a virtual penetrating mirror virtually disposed within the first view of the tangible object, the virtual penetrating minor showing a second view including a reflected image of the tangible object according to a localized position of the displaying device relative to the tangible object as determined by the tracking system.

21. The method for visualizing a virtual object within an augmented reality environment according to claim 20, further comprising:
    registering the reflected second view to the tangible object; and
    superimposing the reflected second view on the tangible object.

22. The method for visualizing a virtual object within an augmented reality environment according to claim 20, further comprising displaying another virtual mirror in the first view.

23. A method for visualizing a virtual object within an augmented reality environment comprising:
    localizing a tangible object relative to a tracking system;
    localizing a tracked interaction device relative to the tracking system; and
    displaying by a displaying device a first view of the tangible object and a virtual penetrating mirror virtually disposed within the first view of the tangible object, the virtual penetrating minor showing a second view including a reflected image of the tangible object according to a localized position of the displaying device relative to the tangible object as determined by the tracking system.

* * * * *